United States Patent
Brevoord et al.

(10) Patent No.: US 7,781,619 B2
(45) Date of Patent: Aug. 24, 2010

(54) PROCESS FOR THE DECARBOXYLATION OF FATTY ACIDS

(75) Inventors: Eelko Brevoord, Amersfoort (NL); Stephan Janbroers, Diemen (NL); Francisco René Mas Cabre, Amstelveen (NL); Mark Hendrikus Harte, Zaandam (NL)

(73) Assignee: Albemarle Netherlands B.V., Amsterdam (NL)

( * ) Notice: Subject to any disclaimer, the term of this patent is extended or adjusted under 35 U.S.C. 154(b) by 0 days.

(21) Appl. No.: 11/717,845

(22) Filed: Mar. 14, 2007

(65) Prior Publication Data

US 2007/0244343 A1    Oct. 18, 2007

(30) Foreign Application Priority Data

Mar. 20, 2006   (EP)   ................... 06075689

(51) Int. Cl.
*C07C 45/41* (2006.01)
*C07C 45/65* (2006.01)

(52) U.S. Cl. ............ 568/354; 568/355; 568/397

(58) Field of Classification Search ............ 568/354, 568/355, 397
See application file for complete search history.

(56) References Cited

U.S. PATENT DOCUMENTS 4,218,386 A * 8/1980 Logan et al. ............. 554/160

5,164,497 A * 11/1992 King et al. ............. 544/87

FOREIGN PATENT DOCUMENTS

GB      836205      6/1960
SU      427728 A    10/1974

OTHER PUBLICATIONS

Kulamani Parida, et al; "Mg/Al Hydrotalcites: Preparation, Characterisation and Ketonisation Of Acetic Acid"; Journal of Molecular Catalysis A:Chemical; 1999; pp. 185-192; vol. 151; 2000 Elsevier Science B.V.; Amsterdam, Netherlands.
Glinski, M., et al., "Ketones From Monocarboxylic acids: Catalytic Ketonization Over Oxide Systems", Applied Catalysis A: General 128 (1995), pp. 209-217.
Nagashima, O., et al., "Ketonization of Carboxylic Acids Over CeO2-based Composite Oxides" , Journal of Molecular Catalysis A: Chemical 227 (2005), pp. 231-239.
Sels, B., et al., "Hydrotalcite-like Anionic Clays in Catalytic Organic Reactions", Catalysis Reviews 43(4), 2001, pp. 443-488.

* cited by examiner

*Primary Examiner*—Sikarl A Witherspoon
(74) *Attorney, Agent, or Firm*—Jeremy J. Kliebert; James A. Jubinsky; Marcy M. Hoefling

(57) ABSTRACT

A process for the production of a ketone having a carbon number between about 20 and about 40 comprising contacting fatty acids containing from about 10 to about 21 carbons atoms with a hydrotalcite catalyst under conditions effective to decarboxylate said acids. More particularly said decarboxylation conditions comprise: a temperature in the range between about 300° C. and about 400° C.; a pressure in the range between about 0.01 and about 5 bar; and a weight hourly space velocity (WHSV) of from about 0.1 to about 10 hr$^{-1}$.

16 Claims, No Drawings

PROCESS FOR THE DECARBOXYLATION OF FATTY ACIDS

This Application claims priority to EP Application No. 06075689.7 filed on Mar. 20, 2006

This invention is directed to the production of ketones from carboxylic acids. More particularly, it is directed to a process for the production of ketones having carbon numbers greater than about 20 by contacting fatty acids with a hydrotalcite catalyst under conditions effective to decarboxylate the fatty acids.

Commercial attention has recently been drawn to the use of vegetable oils and animal fats as sources of useful hydrocarbon products. Most natural fats and oils are complex mixtures of individual triglycerides; these chemical species comprise glycerides in which the glycerol is esterified with three fatty acids of which the chain length can be from about 4 to about 22 carbon atoms, but is more commonly between about 16 and about 18. The term "fatty acid" is herein used to mean carboxylic acid acids corresponding to the carboxylic acid moieties of the triglyceride reactants. The natural fatty acids found in plants and animals typically comprise only even numbers of carbon atoms due to the way they are bio-synthesised from acetly CoA. Bacteria, by contrast, possess the ability to synthesise odd- and branched-chain fatty acids. Consequently, ruminant animal fat can contain significant proportions of branched-chain fatty acids due to the action of bacteria in the rumen.

Historically, the reaction of alkali metal hydroxides with triglycerides (saponification) has long been used for the manufacture of soap and detergents. Furthermore, the trans-esterifcation of triglycerides to form mono-alkyl esters of the fatty acids chains is the central reaction in the production of biodiesel, an increasingly employed alternative to petroleum-based diesel fuel. While the chemistry of hydrolyzing triglycerides to release the constituent fatty acid chains is generally known—being in effect the reverse reaction to the enzymatic biosynthesis of triglycerides in vivo—the potential for further conversion of these carboxylic acid moeities has not been broadly investigated.

One embodiment of the invention is directed to the derivation of utile ketones having carbon numbers greater than about 30 from carboxylic acid moeities by controlled decarboxylation. The decarboxylation of fatty acids in the presence of homogeneous catalysts such as lead tetracetate has been widely proposed in the literature. The heterogeneous pathway—which could allow decarboxylation without chemical activation of the fatty acids—has not been studied extensively by comparison.

UK Patent Application No. 836,205 (Armour and Company) describes a method of catalytically decarboxylating fatty acids, having between 8 and 22 carbon atoms, by contacting said acids with brucite containing at least 5 weight percent silica to form both aldehydes and ketones. Although stearone, palmitone and caprylone may be formed as reaction products, they do not constitute more than 15 weight percent of the total products that are otherwise dominated by highly asymmetrical methyl ketones having from 13 to 18 carbon atoms. This citation suggests the use of brucite as a catalyst due to its natural mineral abundance but acknowledges that it is does not provide any advantages in terms of catalyst life or reaction efficiency compared to magnesium oxide pellets.

U.S. Pat. No. 5,164,497 (King et al.) describes a two-step process in which i) an active hydrogen-containing compound is contacted with a carbon dioxide synthon under conditions effective to produce a carboxylated compound, and ii) contacting said carboxylated compound with a metal oxide catalyst under conditions effective to decarboxylate the carboxylated compound. The metal oxide catalyst for step ii) may comprise exchangeable anionic clay materials such as hydrotalcites and the two-step process may be used to derive ketones (although no chain lengths of these species are disclosed in this document). However, the active hydrogen compound used in step i) is necessarily an organic compound and preferably an alcohol.

Parida et al. [Journal of Molecular Catalysis A: Chemical 151 (2000) 185-192] describes the use of hydrotalcite in the ketonisation of acetic acid, wherein the catalytic activity is optimized by controlling the Mg:Al ratio of the hydrotalcites. The specific teaching of this document is not applied to longer chain acids nor, in particular, to acids of comparative chain length and/or structure to fatty acids. Furthermore, Sels et al. [Catalysis Reviews, 43(4), 443-488 (2001)] questions the value and further application of the teaching of Parida et al.

There is therefore a need in the art to provide a process for the efficient conversion of fatty acids to ketones having a carbon number greater than 30.

DESCRIPTION OF THE INVENTION

In accordance with one embodiment of the invention, there is provided a process for the production of a ketone having a carbon number between about 20 and about 40 comprising contacting fatty acids containing from about 10 to about 21 carbons atoms with a hydrotalcite catalyst under conditions effective to decarboxylate said acids. The hydrotalcite catalyst has been found to be very resistant to the leaching out of cations by fatty acids and water under decarboxylation conditions.

Said fatty acids may be characterized by the general formula R—COOH where R constitutes a hydrocarbon residue having from about 9 to about 20 carbon atoms, preferably from about 15 to about 20 carbons atoms. In accordance with one preferred embodiment of the invention, R constitutes a hydrocarbon of low olefinicity, more preferably a hydrocarbon moiety having $\leq 2$ carbon-carbon double bonds.

The process of the invention has been found to be highly efficient in the conversion of fatty acids to symmetrical ketones. Without being bound by theory, the reaction that occurs over the catalyst constitutes a dimerisation in which carbon dioxide and water are split off. Equation 1 below illustrates this proposed mechanism for a single fatty acid source:

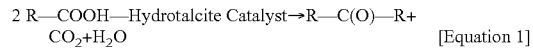

$$2\ R\text{—COOH} \xrightarrow{\text{Hydrotalcite Catalyst}} R\text{—C(O)—R} + CO_2 + H_2O \quad \text{[Equation 1]}$$

In accordance with one preferred embodiment of the invention, the decarboxylation reaction is characterized by achieving a percentage conversion of the carboxylic acids to ketones of greater than about 70%, and more preferably greater than about 85%.

Suitable decarboxylation conditions for the performance of this invention comprise: a temperature in the range between about 225° C. and about 500° C.; a pressure in the range between about 0.01 and about 10 bar, a weight hourly space velocity (WHSV) of from about 0.1 to about 20 hr$^{-1}$.

Furthermore, it is possible for said fatty acids to be contacted with the hydrotalcite catalyst in the presence of inert fluid diluent. Suitable gaseous in this regard may be selected from the group consisting of nitrogen, methane, hydrogen, carbon monoxide or mixtures thereof, but of which nitrogen is the most preferred. Suitable liquid diluents may be selected from the group consisting of benzene, toluene, xylene, ethylbenzene, anisole, heptane, octane, nonane, decane, dibutyl ether and mixtures thereof. Where a diluent is employed, it is preferred that the molar ratio of said diluent to said fatty acid being in the range from about 1 to about 20.

In accordance with one preferred embodiment of the invention, said fatty acids are contacted with the hydrotalcite catalyst when in the gas phase in the presence of nitrogen gas diluent, the molar ratio of said diluent to said fatty acid being in the range from about 5 to about 15, and wherein said decarboxylation conditions comprise: a reaction pressure in the range from about 1 to about 5 bar; a temperature in the range from about 275° C. to about 450° C.; and, a weight hourly space velocity (WHSV) of about 0.1 to about 3 hr$^{-1}$.

In accordance with another embodiment of the invention, there is provided a process for the production of a ketone having a carbon number between about 30 and about 40 comprising: a) hydrolyzing a triglyceride having constituent carboxylic acid moieties containing from about 16 to about 21 carbon atoms to form glycerol and fatty acids corresponding to said carboxylic acid moieties; b) contacting said fatty acids with a hydrotalcite catalyst under conditions effective to decarboxylate the carboxylic acids.

In accordance with one preferred embodiment of the invention, said hydrolysis reaction occurs in the presence of a displacing acid catalyst, a strong acid catalyst and sufficient water to form water and oil phases. Preferably, said displacing acid catalyst is selected from the group consisting of formic acid, acetic acid and propionic acid. Equally, it is preferred that the strong acid catalyst comprises sulphuric acid.

It is strongly preferred that said hydrolysis occurs at a temperature in the range from about 50° C. to about 180° C., in the presence of: a strong acid catalyst; and, a displacing acid catalyst selected from the group consisting of formic acid, acetic acid and propionic acid.

Hydrotalcites belong to a class of layered double hydroxides, having a structure, which is capable of receiving various anions or molecules into the spacings between the respective layers. They are said to exhibit an anion-exchanging property. According to the Journal of the Chemical Society of Japan, 1995, No. 8, pp. 622 to 628, hydrotalcites may be represented by the (charge balanced) general formula:

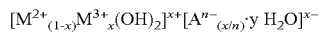

wherein $M^{2+}$ is a divalent metal ion such as $Mg^{2+}$, $Co^{2+}$, $Ni^{2+}$ or $Zn^{2+}$; $M^{3+}$ is a trivalent metal ion such as $Al^{3+}$, $Fe^{3+}$ or $Cr^{3+}$; $A^{n-}$ is an n-valent anion such as $OH^-$, $Cl^-$, $CO_3^{2-}$ or $SO_4^{2-}$; and x is usually 0.1 to 0.33. As such, hydrotalcites have a laminated crystal structure which comprises two-dimensional main layers—composed of regular metal hydroxide octahedral which share edges to form infinite sheets—which possess a positive charge, and interlayers each having a negative charge. Of the possible chemical structures for hydrotalcite particles, Mg—Al-based hydrotalcites—containing layers of magnesium and aluminium hydroxide octahedral—have become prevalent due to their thermal stability and resistance to thermal discoloration.

A general method of producing hydrotalcite comprises mixing an aqueous metal salt solution containing the requisite divalent and trivalent metal ions with an aqueous solution of carbonate ions (from which the anionic interlayers will be derived); the thus obtained mixture is subjected to a co-precipitation reaction under controlled conditions of temperature, pressure and pH. In order to obtain hydrotalcite particles having a particular plate surface diameter or thickness, it is necessary to use more specific reaction conditions, such as those employed in hydrothermal synthesis and the like. Cavani, et al (Catalysis Today 11(2), 1991, 203), International Patent Application Publication Nos. WO1993/03903 (Preston) and WO2004/056705 (Council of Scientific and Industrial Research), Chinese Patent Application No. CN 1600690 (Ying et al.) and Japanese Patent No. 2005060164 (Nittetsu Mining Company) disclose further methods for the preparation of hydrotalcites and the component bimetallic layering thereof using a plurality of different techniques and/or metal sources; their disclosures are herein incorporated by reference.

In accordance with one preferred embodiment of the invention, the hydrotalcite is characterized by having a Mg:Al ratio in the range from about 3.5 to about 4.0, more preferably about 3.7 to about 3.9; and an interlayer spacing in the range from about 3 to about 4 angstroms. Further, it is preferable that the porosity of the catalyst is in the range from about 0.5 cc/g to about 0.7 cc/g, more preferably about 0.7 to about 0.8 cc/g and the density of the catalyst is in the range from about 0.5 to about 0.6 g/cm$^3$.

In accordance with one further embodiment of the invention, metals from Group VIII of the periodic table may be supported on the surface of the hydrotalcite to provide an additional active metal component. Said metals are typically provided in their oxide or sulphided state and preferably said metals are selected from the Group consisting of Mn, Fe, Co, Ni, Pd, Pt and mixtures thereof. The inclusion of said additional component should promote rather than inhibit the decarboxylation pathway and where applicable the "dimerization" pathway shown in Equation 1 above. It is preferred that these metals are included such that they comprise between about 0.1 and about 5 wt.% (calculated as oxides) based on the total weight of said metals and the hydrotalcite.

Fatty acids having between about 16 and about 21 carbon atoms are prevalent from both industrial and natural sources. It is envisaged that the process may be applied to both saturated and unsaturated fatty acids, which in turn may be substituted or unsubstituted. However, it is preferable that the acids contacted with the hydrotalcite catalyst comprise greater than about 50%, more preferably greater than about 75% and most preferably greater than about 90% saturated fatty acids. Preferably, the saturated fatty acids comprise palmitic, stearic, arachidic acids and mixtures thereof.

When unsaturated acids are present in the fatty acid source (or "feed"), it is preferable that such acids are monounsaturated, such as oleic acid. Preferably the fatty acids should comprise less than about 10 mol. %, more preferably less than about 5 mol. % and most preferably less than about 1 mol. % polyunsaturated fatty acids.

The fatty acids may be contacted with the Mg—Al hydrotalcite in the liquid or vapor or supercritical liquid states or mixtures thereof. In this context, the vapor phase reaction is intended to refer to the general vapor state of the starting materials and is the preferred method of performing this step of the invention.

The decarboxylation reaction can be conducted in the presence of at least one inert gaseous diluent. Suitable gaseous diluents that should not prevent the preparation of the desired ketones include nitrogen, methane, hydrogen and carbon monoxide; of these nitrogen and hydrogen are the most preferred. In certain circumstances, nitrogen and hydrogen have been shown to be useful diluents either in increasing the selectivity of the reaction to the particular products desired and/or in limiting catalyst degradation. When a liquid diluent is employed, it should preferably be a good solvent for the starting materials, inert under reaction conditions, and easily separable from the ketone product. If separation by distillation is to be performed, the diluent may be a liquid that does not form an azeotropic mixture with the ketone and of which the boiling point is adequately separated from that of the ketone. In that regard, useful diluents include benzene, toluene, xylene, ethylbenzene, anisole, heptane, octane, nonane, decane, dibutyl ether, and the like.

The degree of dilution of the carboxylic acids may vary considerably depending upon any process constraints restricting the use of the diluent. For example, the use of large quantities of gaseous diluents may be disadvantageous due to the energetic cost of pumping such volumes and the increased difficulty in isolating the ketone product. Consequently, where gaseous diluents are used, it is preferred that the carboxylic acids constitute between about 1 and about 95 mole percent of the starting material/carrier feed, and more preferably between about 5 and about 50 mole percent thereof. Where liquid diluents are used, it is preferred that that the diluent comprises between 1 and 90 wt % (based on the total weight of the carboxylic acid and diluent) and more preferably between about 5 and about 50 wt.% thereof.

Where the acids are to contact the Mg—Al hydrotalcite when in the gas phase, the raw materials are typically fed into a vaporizer, where the acid will also be admixed with any gaseous diluent. This diluent will here act to drive the evaporation of the fatty acid. The fatty acid and/or diluent are preferably heated before entering the vaporizer and additionally the exit flow of fatty acid and diluent from the vaporizer is preferably further heated to prevent it cooling to a temperature below that of the vaporizer.

The fatty acid raw material, together with the diluent when used, is contacted with the Mg—Al hydrotalcite in a so-called reaction zone. Such a zone may, for example, be contained within a fixed bed reactor, a fluid bed reactor, or a slurry reactor. The decarboxylation processes can also be conducted in a glass-lined stainless steel or similar type reaction equipment. It is preferable that the reaction zone may be fitted with one or more internal and/or external heat exchangers in order to control undue temperature fluctuations, and to prevent any possible "runaway" reaction temperatures.

The decarboxylation reaction conditions may range from subatmospheric or atmospheric to superatmospheric conditions, it is desirable to run the step (ii) reaction at a pressure between about 0.1 and about 10 bar, and preferably between about 1 and about 5 bar. The weight hourly space velocity (WHSV), defined as the mass flow of fatty acid per hour per kilogram of catalyst is preferably in the range from about 0.1 to about 20 $hr^{-1}$, more preferably about 0.1 to about 10 $hr^{-1}$.

The temperature of decarboxylation step is generally selected to be in the range from about 150° C. to about 500° C. but is preferably from about 225° C. to about 425° C., and more preferably from about 300° C. to about 400° C. At this temperature it is possible that fatty acids can undergo cracking or pyrolysis; however these unwanted reactions are minimized through the choice of hydrotalcite as the decarboxylation catalyst (and the selection of the appropriate processing conditions as would be apparent to a man of ordinary skill in this art).

The residence time will be that period sufficient to produce the decarboxylated compound products which is inter alia dependent on the temperature and pressure of the reaction, the type of carboxylic acid, and the proportion of diluents in the materials to be contacted with the hydrotalcite. Generally the reaction time will be in the range from about 0.5 to about 100 hours, but is preferably from 1 to 10 hours.

The product of the decarboxylation is removed from the reaction zone, preferably as a continuous stream. Any ketones derived by decarboxylation can be separated from by-products (such as oligomeric or polymeric species and low molecular weight "fragments" from the fatty acid chains) by distillation. For example, the crude reaction product can be subjected to a distillation-separation at atmospheric or reduced pressure through a packed distillation column.

Derived ketones having between about 31 and about 41 carbon atoms are solids at room temperature and pressure. In order to prevent clogging of the apparatus in which the decarboxylation is performed, it may be necessary to heat those tubes by which the decarboxylation product is removed from the reaction zone and any vessel into which the ketones are to be collected.

In accordance with one preferred embodiment of the invention, the reactant to be decarboxlyated is derived by hydrolyzing a triglyceride having constituent carboxylic acid moieties containing from about 16 to about 21 carbon atoms to form glycerol and carboxylic acids corresponding to said carboxylic acid moieties.

The triglyceride reactants are preferably of biological origin and in particularly are derived from naturally occurring animal, fish and vegetable fats. It is known that triglycerides from fish and animal oils contain acids with chain lengths that normally exceed 15 carbon atoms and usually contain large amounts of mono- and poly-unsaturated acids. Equally, triglycerides from some plant species contain appreciable amounts of shorter chain acids, having 10, 12 or 14 carbon atoms which tend to be mainly saturated acids. A person of ordinary skill in the art would therefore be aware of the appropriate animal, fish and vegetable oils to be used (alone or in combination) in order to derive carboxylic acid moieties as required by the present invention.

In this regard, useful sources (which may be used alone or in combination) include coconut oil, palm oil, palm kernel oil, safflower oil, sesame oil, soybean oil, rapeseed oil, corn oil, mustard oil, sunflower oil, yellow grease, trap grease, lard, edible tallow, inedible tallow and mixtures thereof. Of these, the most preferred source is rapeseed oil.

The quality of such oils and greases as a source of fatty acids is often related to the amount of free fatty acid (FFA) which is contained within the oil in addition to the utile triglyceride molecules. [The free fatty acids (FFA) may have themselves broken off the triglyceride.] However, other impurities such as trace metals, phosphatides, carotenoids, aflotoxins, biocides and polychlorinated hydrocarbons which may also be present in such oils. Therefore, depending on the grade and preparation of the animal and vegetable oils, it may be necessary to pre-treat them to remove the free fatty acids and these impurities.

The pre-treatment process actually applied will of course depend on the type of oil used but will generally comprise at least one process selected from the group consisting of degumming, deodorization (vacuum distillation), steam stripping, caustic stripping, solvent extraction and bleaching.

When triglycerides and water are admixed, the resultant reaction mixture is heterogeneous in that it comprises oil and water phases. It is imperative to this reaction step that the amount of water used is sufficient to result in the formation of the two liquid layers—the oil phase overlying the bottom water phase—if the reaction mixture was not subjected to agitation. As the hydrolysis reaction proceeds, the products will partition between the two phases, the oil phase containing the carboxylic acid products and low levels of mono- and di-glyceride impurity and the water phase containing glycerol. This partitioning impacts on the equilibria in the water and oil phases and contributes to driving the reaction to completion.

To further enhance the rate of the hydrolysis reaction, the triglycerides and water may be admixed under conditions of high temperature ($\geq 250°$ C.) and pressure (700 psi). However, would necessitate the use of expensive equipment. Preferred reactions conditions are described in U.S. Pat. No. 4,218,386 (Proctor and Gamble) which is herein incorporated by reference. This citation describes the use of a strong acid catalyst and a displacing acid catalyst to promote the hydrolysis reaction. In this case, the amount of water employed must to be enough to cause the aforementioned formation of oil and water phases. (What amount this is, is dependent on the triglyceride reactant and displacing acid catalyst.) This phase formation is important because of the function indicated above for the water phase which result in fast relatively complete reaction and formation of glycerine rather than glyceride (e.g. triacetin).

Preferably, the displacing acid catalyst is selected from the group consisting of formic acid, acetic acid and propionic acid. Although a person of ordinary skill in this art would be aware of a number of suitable strong acid catalysts, it is preferred to use sulphuric acid in this capacity.

The use of these catalysts enables lower temperatures to be employed in the achievement of a utile rate of hydrolysis. It is preferred that the catalyzed hydrolysis reaction occurs at a temperature between about 50° C. and about 180° C. and more preferably between about 60° C. and about 150° C.

Without being bound by theory, the water is believed to have a three roles in this catalysed hydrolysis reaction. Firstly, water may act as a promoter for the strong acid catalyst which drives the acidolysis of the of triglycerides; secondly, provided it is present in a sufficient amount, it serves to provide a water phase which functions to extract water-soluble glyceride and thereby drive the triglyceride solubilization reaction toward completion and, thirdly, it reacts to hydrolyze water-soluble glyceride to produce glycerine and carboxylic acids corresponding to carboxylic acid moieties of triglyceride reactant, and to release displacing acid to function in the triglyceride solubilizing step.

In the described hydrolysis reactions, water is used in an amount such that the weight percentage of water based on triglyceride reactant ranges from about 5% to about 100%. However, it is preferable that water comprises greater than about 10% by weight of the reaction mixture.

With respect to the acid catalyzed hydrolysis the amount of water added has to be controlled to avoid excess dilution of the catalysts. A person of ordinary skill in the art would be capable of selecting appropriate quantities and concentrations of displacing acid catalyst, strong acid catalyst and feedstock (triglyceride source) to be added to a given amount of water to cause the formation of requisite oil and water phases.

Following the hydrolysis reaction, the carboxylic acids—having between 16 and 21 carbons atoms—are readily obtained from the oil phase layer by either simple distillation or water washing and distillation. If required glycerol—and any other relevant constituents—can be recovered from the water phase by neutralization followed by distillation.

The hydrolysis step of this invention may be carried out in any one of several different contacting patterns. Batch processes, for example, may include both single stage and multistage processes, the latter involving reacting a first batch triglyceride in a vessel until the rate of hydrolysis becomes slow, separating the oil phase therefrom and then refreshing the reactants. For batch processing in general, suitable equipment consists of a reaction vessel or pot equipped with an agitator. For continuous processing, a suitable reactor may comprise a tube of sufficient length to provide intimate contact between the oil and water phases for a satisfactory residence time. Alternative continuous processing systems can involve a series of stirred tank reactors, plug flow reactors or countercurrents systems. Such continuous systems can include a plurality of locations in which to introduce the reactants.

The decarboxylation reaction of this invention, together with the hydrolysis step where utilized, can be conducted in a batch or continuous fashion, with recycling of unconsumed starting materials if required. In either case, it is preferable to employ a suitable means for introducing and/or adjusting the quantity and relative molar ratios of the starting materials.

The ketones derived in the process of this invention—whether separated by distillation from the product of decarboxylation or otherwise—may themselves be used for a plurality of purposes or may be subjected to further processing to derive other useful products. Ketones can find use as solvents, flavourants and odours for example, but interest is increasing in the use of ketones in medical treatment [into Parkinson's disease and diabetes in particular], in biomimetic surfaces [following the realization that ketones are prevalent in the epicuticular wax of many angiosperms] and as a bulk foodstuff [in the so-called ketogenic diet].

In accordance with one preferred embodiment of the invention, the derived ketones are subjected to further processing comprising at least the hydrodeoxygenation of said ketones.

The following example further illustrates the preparation and use of the catalyst system according to the invention.

EXAMPLE

Hydrotalcite having an $MgO/Al_2O_3$ ratio of 3.7 was used as the decarboxylation catalyst. The catalyst was retained in an electrically heated tube having a diameter of 3.4 cm and height of 153 cm. The catalyst bed section of the tube measured approximately 850 ml and was filled with approximately 500 g of the hydrotalcite. This section was contained within two glass pearl sections which were 15 cm and 30 cm high for the positions below and above the catalyst bed respectively. The pearls had a diameter between 3 and 4 mm. A first thermocouple was retained in the upper layer of the glass pearls just above the catalyst bed. Three further thermocouples were divided over the catalyst bed.

The raw material acid used was stearic acid provided under the product name Kortacid 1895, available from Akzo Nobel Chemicals GmbH. 96.9 mole % of said product was saturated C18 carboxylic acid and the total constituent of C16-C20 carboxylic acids 99.2 mole %.

Prior to decarboxylation, the fatty acid was retained in a molten state in a storage tank. From this tank the fatty acid was pumped into a vaporizer whilst concomitantly being heated. Within the vaporizer the fatty acid was admixed with a pre-heated flow of nitrogen that was used as the driving gas for the evaporation of the acid. The temperature of the vaporizer was controlled such that there was a pitch flow of 5 to 15%, the pitch being withdrawn with a suitable pump. The vapour stream, of which the flow was also controlled by the temperature of the vaporizer, was transported to the catalyst bed through an electrically heated tube of which the temperature approximated to that of the catalyst bed. The feed of vaporized fatty acid and nitrogen diluent was then introduced into the top portion of the tube retaining the catalyst.

In summary, the following process conditions were employed:

TABLE 1

| Condition | |
| --- | --- |
| Temperature of Catalyst Bed (° C.) | 384 |
| Feed Flow (g/min) | 4.0 |
| Nitrogen Flow (Nl/min) | 3.2 |
| Pitch (% of Feed) | 15 |
| X-ratio* | 10 |
| WHSV (hr$^{-1}$) | 0.47 |

*Xratio: [(No. moles nitrogen)/(No. moles fatty acid)] in gas stream entering the catalyst bed.

The fatty acid was converted to ketone, water and carbon dioxide. After the catalyst bed, the product was partly condensed in a first condenser; the resultant liquid part was pumped to a product tank. The remaining vapor stream (mainly water and light ends) was passed through a second condenser; the liquid part was collected in a tank, the off-gas was scrubbed with water and vented off. [As C35 ketone is a solid at room temperature and pressure, the product tank was heated to retain it in a liquid state (and avoid clogging of the apparatus).]

The product was analyzed using three techniques:
a) Fatty Acid Titration: The unreacted fatty acid content is analyzed by titration with NaOH. For the analysis, a molecular weight of 285 was used for the stearic acid in order to calculate the amount in wt. %.
b) $^1$H-NMR: This is used to determine: i) the ratio of $CH_2$—C=O (ketones): $CH_3$ (end group) for the yield of ketone and ii) the ratio of $CH_2$—C=O (fatty acid): $CH_3$ (end group) to determine the conversion of fatty acid.
c) HSPEC: This analysis is a separation based on molecular weight and is used to determine the content of the products with a molecular weight of C35 ketone.

The following table illustrates the results of these analyses:

TABLE 2

| Analysis | Condition Analyzed | Result |
| --- | --- | --- |
| Titration | Residual Fatty Acid (wt. %) | 7 |
| HPSEC (all values in % area) | Fatty Acid | 3.6 |
| | C35 Ketone | 86.9 |
| | Oligomer and Polymer | 5.6 |
| | Unknown Products of molecular weight between Ketone and fatty acid | 1.2 |
| | Unknown Product with molecular weight lower than fatty acid | 2.7 |

From the foregoing it is clear that the present invention provides an efficient process for the conversion of fatty acids to longer chain ketones, and in particular a highly efficient process for the conversion of fatty acid to symmetrical ketones.

It is understood that various other embodiments and modifications in the practice of the invention will be apparent to, and can be readily made by, those skilled in the art without departing from the scope and spirit of the invention described above.

The invention claimed is:

1. A process for the production of a ketone having a carbon number between 20 and 40 comprising contacting fatty acids containing from 10 to 21 carbons atoms with a hydrotalcite catalyst under conditions effective to decarboxylate said acids, wherein said fatty acids comprise greater than about 90% saturated fatty acids.

2. A process for the production of a ketone having a carbon number between and 20 and 40 comprising:
   a) hydrolyzing a triglyceride having constituent carboxylic acid moieties containing from 10 to and 21 carbon atoms to form glycerol and fatty acids corresponding to said carboxylic acid moieties, and
   b) contacting said fatty acids with a hydrotalcite catalyst under conditions effective to decarboxylate the carboxylic acids,
   wherein said fatty acids comprise greater than about 90% saturated fatty acids.

3. A process according to claim 1, wherein said fatty acids substantially comprise saturated fatty acids.

4. A process according to claim 3, wherein the hydrolyzing reaction of a) occurs in the presence of a displacing acid catalyst, a strong acid catalyst and sufficient water to form water and oil phases.

5. A process according to claim 4, wherein said displacing acid catalyst is selected from the group consisting of formic acid, acetic acid and propionic acid.

6. A process according to claim 5, wherein the strong acid catalyst comprises sulphuric acid.

7. A process according to claim 4, wherein the hydrolyzing reaction of a) occurs at a temperature in the range from about 50° C. to about 180° C.

8. A process according to claim 4, wherein said decarboxylation reaction is characterized by achieving a percentage conversion of the fatty acids to ketones of greater than about 85%.

9. A process according to claim 4, wherein said decarboxylation conditions comprise: a temperature in the range between about 300° C. and about 400° C.; a pressure in the range between about 0.01 and about 5 bar; and a weight hourly space velocity (WHSV) of from about 0.1 to about 10 $^{-1}$.

10. A process according to claim 4, wherein said fatty acids are contacted with the hydrotalcite catalyst in the presence of inert gaseous diluent, the molar ratio of said diluent to said fatty acid being in the range from about 1 to about 20.

11. A process according to claim 10, wherein said diluent is a gas selected from the group consisting of nitrogen, methane, hydrogen, carbon monoxide or mixtures thereof.

12. A process according to claim 1, wherein said fatty acids are contacted with the hydrotalcite catalyst when in the gas phase in the presence of nitrogen gas diluent; the molar ratio of said diluent to said fatty acid being in the range from about 5 to about 15; and wherein said decarboxylation conditions comprise: a reaction pressure in the range from about 1 to about 5 bar; a temperature in the range from about 300° C. to about 400° C.; and, a weight hourly space velocity (WHSV) of about 0.1 to about 3 hr$^{-1}$.

13. A process according to claim 1, wherein the hydrotalcite catalyst has a Mg:Al ratio in the range from about 3.5 to about 4.0 and an interlayer spacing in the range from about 3 to about 4 angstroms.

14. A process according to claim 1, wherein the hydrotalcite catalyst supports on its surface a metal component comprising metals selected from the group consisting of Mn, Fe, Co, Ni, Pd, Pt and mixtures thereof such that said metal component comprises between about 0.1 and about 5 wt.% (calculated as oxides) based on the total weight of the metal component and the hydrotalcite.

15. A process according to claim 1, wherein the fatty acids dimerize to form a symmetrical ketone.

16. A process according to claim 15, wherein the reaction is characterized by achieving a percentage conversion of the fatty acids to the ketone of greater than about 70%.

* * * * *